United States Patent
Kang et al.

(10) Patent No.: US 9,867,868 B2
(45) Date of Patent: Jan. 16, 2018

(54) PHARMACEUTICAL COMPOSITION FOR TREATING OR PREVENTING CORNEAL WOUND COMPRISING THYMOSIN β4 AND CITRIC ACID

(71) Applicant: G-treeBNT CO., LTD., Seongnam-si, Gyeonggi-do (KR)

(72) Inventors: Sin Wook Kang, Seongnam-si (KR); Kyoungsun Kim, Busan (KR); Ji Hye Sung, Seoul (KR)

(73) Assignee: G-TREEBNT CO., LTD., Seongnam-si (KR)

( * ) Notice: Subject to any disclaimer, the term of this patent is extended or adjusted under 35 U.S.C. 154(b) by 0 days.

(21) Appl. No.: 14/844,421

(22) Filed: Sep. 3, 2015

(65) Prior Publication Data
US 2017/0049857 A1    Feb. 23, 2017

(30) Foreign Application Priority Data
Aug. 18, 2015    (KR) .................. 10-2015-0116089

(51) Int. Cl.
| | |
|---|---|
| A61K 38/22 | (2006.01) |
| C07K 14/575 | (2006.01) |
| A61K 9/00 | (2006.01) |
| A61K 31/194 | (2006.01) |
| A61K 31/19 | (2006.01) |
| A61K 47/02 | (2006.01) |
| A61K 9/08 | (2006.01) |

(52) U.S. Cl.
CPC ........ *A61K 38/2292* (2013.01); *A61K 9/0048* (2013.01); *A61K 9/08* (2013.01); *A61K 31/19* (2013.01); *A61K 31/194* (2013.01); *A61K 47/02* (2013.01)

(58) Field of Classification Search
CPC ............ A61K 2300/00; A61K 38/2292; A61K 38/00; A61K 38/32; C07K 14/57581
See application file for complete search history.

(56) References Cited

U.S. PATENT DOCUMENTS 8,383,576 B2 * 2/2013 Crockford ............ A61K 9/0048
514/1.1

OTHER PUBLICATIONS

Pfister et al., Invest. Ophthalmol. Vis. Sci., 1981, 486-490.*

* cited by examiner

*Primary Examiner* — Kaipeen Yang
(74) *Attorney, Agent, or Firm* — Sughrue Mion, PLLC

(57) ABSTRACT

The present invention relates to a composition for the treatment or prevention of a corneal injury, which comprises thymosin β4, and citric acid or its salt as active ingredients. The composition may further comprise at least one organic acid selected from acetic acid, ascorbic acid or salts thereof. The composition can maintain or increase the activity of thymosin β4 conventionally used to effectively treat wounds on the cornea, and thus, is useful as an ophthalmic formulation for treating the corneal injury.

12 Claims, 5 Drawing Sheets

PHARMACEUTICAL COMPOSITION FOR TREATING OR PREVENTING CORNEAL WOUND COMPRISING THYMOSIN β4 AND CITRIC ACID

FIELD OF THE INVENTION

The present invention relates to a pharmaceutical composition for treating or preventing corneal injury, comprising thymosin β4 and citric acid as active ingredients.

BACKGROUND OF THE INVENTION

The cornea is a transparent tissue without blood vessels on the front surface of an eyeball, which is often called the dark part of an eye. More particularly, the cornea protects the eye from external conditions, and plays a significant role of refracting and transmitting lights to get a sight of objects. It has well-developed nerve fibers to sensitively respond to foreign substances. The cornea is composed of five layers including a corneal epithelium, Bowman's membrane, corneal stroma, Descemet's membrane and corneal endothelium.

The surface of the cornea is directly exposed to the outside and vulnerable to wound or scratch. Therefore, corneal injuries often occur in patients suffering from ophthalmic diseases such as dry eye syndrome because a shortage of tear drastically deteriorates eyeball protection function of tears. The corneal injuries may cause symptoms such as a feeling of stimulus, a feeling of irritation or dryness and, lead to corneitis when getting worse. Therefore, in order to keep the eyeball healthy and preserve the eyesight, it is necessary to prevent the cornea from being injured, prevent trivial corneal injuries from being worse or treat the injured cornea.

Meanwhile, it is well known that, when the cornea is injured, in particular, by alkali burns, broad infiltration of polymorphonuclear leukocytes (PMN) occurs (Invest. Ophthalmology & Vis. Sci., 1987, 28, pp. 295-304). Such PMN infiltration is part of general inflammatory responses in association with tissue injury. However, in case of the chemical burns of the cornea, PMN infiltration is not only a primary inflammatory response but also leads to ulcer, or may even cause corneal perforation (Trans. Am. Acad. Ophthalmol. Otolaryngol., 1970, 74. pp. 375-383, Invest. Ophthalmology & Vis. Sci., 1979, 18, pp. 570-587). In fact, PMN is known as a major source of collagenase to destroy corneal collagen tissues. Therefore, it is understood that expansion of lesions is stopped by preventing infiltration of PMN, and that the progress of a corneal injury to ulcer may be delayed by inhibiting PMN metabolism. A number of studies have reported that citric acid is effective in reducing PMN infiltration (Exp. Eye. Res., 1984, 39, pp. 701-708).

Meanwhile, thymosin β4 is a protein first discovered in the thymus gland in 1981, which comprises 41 to 43 amino acids and has an isoelectric point of 5.1. In 1991, thymosin β4 was identified by Liva et al. as an actin-sequestering molecule from animal cells, and thereafter, found to be involved in the immune regulation and neuro-endocrine system. Recently, Korean Laid-open Patent Publication No. 10-2008-33939 discloses an eye drop composition comprising thymosin β4 and an amino acid stabilizer, which may further comprise a bulking agent, a buffer and a pH modifier. However, this publication does not describe any desired combination and contents of individual components to optimize or enhance the efficacy of thymosin β4.

As a result of extensive efforts to find out an optimum combination and contents of components, the present inventors have found that a specific organic acid may influence upon the activity of thymosin β4 and a composition containing acid could be used for treating corneal injuries, thereby accomplishing the present invention.

SUMMARY OF THE INVENTION

It is an object of the present invention to provide a composition for treating a corneal injury, comprising thymosin β4 and an organic acid.

In accordance with one aspect of the present invention, there is provided a composition for treating an injured cornea or for preventing a corneal injury, which comprises thymosin β4 and citric acid.

In accordance with another aspect of the present invention, there is provided a composition for treating an injured cornea or for preventing a corneal injury, which comprises thymosin β4, citric acid and acetic acid.

The composition of the present invention comprising thymosin β4 and citric acid promotes migration and proliferation of corneal epithelial cells and inhibits PMN infiltration in the injured cornea so as to facilitate the recovery of the corneal injury, when compared with the use of thymosin β4 alone. Further, the simultaneous use of thymosin β4, citric acid and acetic acid produces superior effects over the use of thymosin β4 alone in terms of cell migration and proliferation, and better effects than the individual use of the components in terms of PMN infiltration. Accordingly, the composition of the present invention enhances the effects of thymosin β4, thereby being useful for the treatment or prevention of corneal injuries.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The present invention provides a composition for the treatment or prevention of a corneal injury, which comprises thymosin β4 and citric acid or its salt as active ingredients.

The term "thymosin β4" as used herein refers to a polypeptide composed of 43 amino acids having 4.9 kDa occasionally called thymosin beta-4 or Tβ4, which was first isolated from thymus and then identified from various tissues. This protein is upregulated during in vitro migration and differentiation of endothelial cells. A number of thymosin β4 iso-types have been identified and found to have homology of about 70% or more, about 75% or more, or about 80% or more with the known amino acid sequences of thymosin β4. Thymosin β4 of the present invention may also be an N-terminal mutant or C-terminal mutant of wild-type thymosin β4. Preferably, thymosin β4 of the present invention refers to the protein having an amino acid sequence of SEQ ID NO: 1.

Citric acid used herein is a compound represented by formula $C_6H_8O_7$. In the present invention, this may also be used in the form of citrate. The citrate indicates derivatives of citric acid including sodium citrate and trisodium citrate. Although citric acid and its salt is generally used as a buffer to reduce a pH change, the present invention needs quite a larger amount of citric acid or its salt than that commonly used in the art. In the present invention, citric acid or its salt may be included in an amount of 1% (w/v) to 15% (w/v) based on the total volume of the composition. Further, citric acid or its salt may be included in an amount of 5% (w/v) to 12% (w/v), preferably 10% (w/v) based on the total volume of the composition.

Further, citric acid or its salt may be used in an amount of 10 to 120 parts by weight per 1 part by weight of thymosin β4. Further, it may be used in an amount of 25 to 100 parts by weight per 1 part by weight of thymosin β4. Preferably, citric acid or its salt may be used in an amount of 50 to 80 parts by weight per 1 part by weight of thymosin β4.

The term "corneal injury" as used herein means a wound on the cornea as the surface of an eyeball, and it may be caused by not only an external impact but also any internal factor in the body. Such a wound may be caused in the corneal epithelium, Bowman's membrane, corneal stroma, Descemet's membrane and/or corneal endothelium.

Further, the composition in accordance with the present invention may further comprise at least one organic acid selected from a group consisting of acetic acid, ascorbic acid and salts thereof.

The acetic acid used herein is a weak acid represented by formula $CH_3COOH$. In the present invention, this may also be used in the form of acetate. One embodiment of the acetate may be sodium acetate.

Further, the ascorbic acid used herein is a weak acid represented by formula $C_6H_8O_6$, which is often called vitamin C. In the present invention, this may also be used in the form of ascorbate. One embodiment of the ascorbate may be sodium ascorbate.

Although, the organic acid and its salt according to the present invention is generally used as a buffer to reduce a pH change or an antioxidant, the present invention needs quite a larger amount of an organic acid or its salt than that commonly used in the art. In the present invention, the organic acid or its salt may be included in an amount of 1.0% (w/v) to 8% (w/v), or 1.5% (w/v) to 5% (w/v) based on the total volume of the composition. Preferably, the organic acid or its salt may be included in an amount of 3.5% (w/v) to 5% (w/v) based on the total volume of the composition.

The organic acid or its salt may be included in an amount of 15 to 100 parts by weight per 100 parts by weight of citric acid or its salt. The organic acid or its salt may be also included in an amount of 15 to 70 parts by weight or 30 to 65 parts by weight per 100 parts by weight of citric acid or its salt. Preferably, the organic acid or its salt may be included in an amount of 40 to 60 parts by weight per 100 parts by weight of citric acid or its salt.

Further, the composition described herein may be prepared into a formulation available for ophthalmic application. Particularly, the formulation may include, for example, solution, lotion, plaster, gel, cream, paste, spray, suspension, dispersion, hydrogel, ointment, oil or foaming agent, or the like. In one embodiment, the present composition comprising thymosin β4 and citric acid may be formulated by being mixed with any pharmaceutically acceptable, in particular, ophthalmically acceptable non-toxic excipients or carriers. For instance, carrier, stabilizer, solubilizer, buffer substrate, preservative, thickener and/or other excipients such as those described below may be used. Further, the solution used herein may be adjusted to have a desired pH value.

The carriers used in the present invention may be typically suitable for topical or systemic administration and may include, for example, water; a mixture of water and water-miscible solvents such as $C_1$-$C_7$ alkanols, vegetable oils or mineral oils such as 0.5 to 5 wt. % of hydroxyethyl cellulose, ethyl oleate, carboxymethyl cellulose, polyvinyl pyrrolidone, and other non-toxic water-soluble polymers for ophthalmic use, for example, cellulose derivatives such as methyl cellulose, alkali-metal salts of carboxymethyl cellulose, hydroxymethyl cellulose, hydroxyethyl cellulose, hydroxypropyl methyl cellulose and hydroxypropyl cellulose, acrylates or methacrylates such as salts of polyacrylate or ethyl acrylate, polyacrylamides; natural products such as gelatin, alginate, pectin, tragacanth, karaya gum, xanthan gum, carrageenin, agar, acacia, starch derivatives such as starch acetate and hydroxylpropyl starch; and other synthetic products, for example, polyvinyl alcohol, polyvinyl pyrrolidone, polyvinyl methylether, polyethylene oxide, preferably, cross-linked polyacrylic acid such as neutral carbopol, or mixtures of the above polymers. Preferable carriers may include water, cellulose derivatives, for example, methyl cellulose, alkali-metal salts of carboxymethyl cellulose, hydroxymethyl cellulose, hydroxyethyl cellulose, hydroxypropyl methyl cellulose and hydroxypropyl cellulose, neutral carbopol, or mixtures thereof.

The stabilizers useable in the composition for ophthalmic use according to the present invention may include, for example, tyloxapol, aliphatic glycerol poly-lower alkylene glycol esters, aliphatic poly-lower alkylene glycol esters, polyethylene glycols, glycerol ethers or mixtures of these compounds. They are typically added in an amount sufficient to dissolve active ingredients.

The buffer useable in the composition of the present invention may include borate, hydrocarbonate/carbonate, gluconate, phosphate, propionate and tromethamine (TRIS) buffers. Tromethamine and borate buffers are preferred. The buffer is added, for example, in an amount to ensure and maintain a physiologically acceptable pH range. Such pH may be typically in the range of pH 5 to 9, preferably pH 6 to 8.2, more preferably pH 6.8 to 8.1.

The preservatives useable in the composition of the present invention may include, for example, quaternary ammonium salts such as Cetrimide, benzalkonium chloride or benzoxonium chloride; alkyl-mercury salts of thiosalicylic acid such as thimerosal, phenylmercuric nitrate, phenylmercuric acetate or phenylmercuric borate, parabens such as phenylparaben or propylparaben, alcohols such as chlorobutanol, benzyl alcohol or phenyl ethanol, guanidine derivatives such as chlorohexidine or polyhexamethylene biguanide or sorbic acid. Preferable preservatives may include cetrimide, benzalkonium chloride, benzoxonium chloride and parabens. The preservative may be added in a sufficient amount to prevent secondary contamination caused by bacteria and fungi during the use.

A tonicity agent may be used in the composition of the present invention for adjusting the composition closer to isotonicity (e.g., 0.9% saline). For instance, sodium chloride, potassium chloride, calcium chloride, dextrose and/or mannitol may be added to the composition comprising thymosin β4 according to the present invention. An amount of the tonicity agent depends upon the kind of active agents to be added. In general, particular compositions of the present invention may include a tonicity agent therein to enable the final composition to have an osmolality acceptable for ophthalmic use, i.e., preferably in a range of 150 to 450 mOsm, and more preferably in a range of 250 to 350 mOsm. Preferable tonicity agents may include, for example, sodium salts and potassium salts, in particular, sodium chloride and potassium chloride. Most preferably, the tonicity agent is sodium chloride.

Further, in order to maintain a proper viscosity in the ophthalmic formulation, the following formulations may be, but not be limited to: (a) monomeric polyols, for example, tyloxapol, glycerol, propylene glycol, ethylene glycol; (b) polymeric polyols, for example, polyethylene glycol (e.g., PEG 300, PEG 400); (c) cellulose derivatives (cellulose-based polymers), for example, hydroxyethyl cellulose, hypromellose, hydroxypropyl methyl cellulose, methyl cellulose, sodium carboxymethyl cellulose, hydroxypropyl cellulose; (d) dextrans, for example, dextran 70; (e) water-soluble proteins, for example, gelatin; (f) vinyl polymers, for example, polyvinyl alcohol, polyvinyl pyrrolidine; (g) other polyols, for example, polysorbate 80, povidone; (h) carbomers, for example, carbomer 934P, carbomer 941, carbomer 940 and carbomer 974P; and (i) polysaccharides/glycosaminoglycans, for example, hyaluronan (hyaluronaic acid/hyaluronate), condroitin sulfate. In addition, at least one viscosity enhancer may be added to the compositions of the present invention, in order to increase the viscosity of the carrier (vehicle).

Although the amount and type of excipient(s) added may be varied depending on specific requirements, the excipient(s) is generally used in a range of about 0.0001 to about 90 wt. %, and within the range commonly used in ophthalmic fields. Further, a pH value of ophthalmic formulations may range from pH 3.5 to 9, preferably from pH 4.5 to 8, and most preferably from pH 5.5 to 7.8, and may be about pH 7.0.

In another aspect of the present invention, there is provided a method for the treatment or prevention of a corneal injury, comprising administering thymosin β4, and citric acid or its salt to a subject.

Further, the present invention provides a treatment method which comprises contacting an eye tissue with an effective amount of a composition comprising thymosin β4 and citric acid as active ingredients. Examples of direct administration may include directly applying to a subject, for example, a solution, lotion, plaster, gel, cream, paste, spray, suspension, dispersion, hydrogel, ointment, oil or foaming agent that contains thymosin β4 described herein, thereby contacting same with tissues.

Further, thymosin β4, and citric acid or its salt may be administered concurrently or sequentially with suitably divided doses several times a day. However, the simultaneous administration of thymosin β4, and citric acid or its salt is most preferred.

An amount of thymosin β4 in the composition may range from 0.05 to 0.5% (w/v) or from 0.1 to 0.4% (w/v) based on the total volume of the composition, which may be administered with a total daily dose of 0.08 to 2.0 ml. It may be administered once a day or with divided doses several times a day, preferably, twice to five times a day. Further, the citric acid or its salt may be included in an amount of 1.5% (w/v) to 10% (w/v) based on the total volume of the composition. Further, it may be administered with a total daily dose of 0.1 to 4.0 ml. Citric acid or its salt may be administered once a day or with divided doses several times a day, preferably, twice to five times a day.

Further, acetic acid, ascorbic acid or salts thereof may be administered concurrently or sequentially along with thymosin β4, and citric acid or its salt. Preferably, the acetic acid, ascorbic acid or salts thereof are administered simultaneously with thymosin β4 and citric acid or its salt. Further, the acetic acid, ascorbic acid or salts thereof may be included in an amount of 1.0% (w/v) to 8% (w/v), or 3.5% (w/v) to 5% (w/v) based on the total volume of the composition, which may be administered with a total daily dose of 0.10 to 4.0 ml. The acetic acid, ascorbic acid or salts thereof may be administered once a day or with divided doses several times a day, preferably, twice to five times a day.

The pharmaceutical composition according to the present invention is preferably administered transdermally (e.g., topically) and may be administered, for example, via parenteral or intranasal (e.g., inhalation) route, or through a mucous membrane, or the like, however, not be particularly limited thereto.

Hereinafter, in order to more clearly understand the present invention, the present invention will be described in more details by the following examples. However, the examples of the present invention may include different variations or modifications and it is not construed that the scope of the present invention is limited within the scope of the following examples.

EXAMPLE 1

Preparation of a Composition Comprising Thymosin β4

Sodium citrate was added in sterile purified water in an amount of 1.5% (w/v) based on the total volume of the composition and mixed to be completely dissolved therein. Then 0.1% (w/v) of thymosin β4 (Bachem., US, SEQ ID No. 1) was added to the mixture and mixed until it was completely dissolved therein. The pH value of the resulting solution was adjusted to pH 7.0 by using sodium hydroxide and hydrochloric acid. Thereafter, the solution was filtered through a 0.2 μm filter, and then, the mixture filtered was filled in a low density polyethylene container, followed by sealing same.

EXAMPLES 2 to 17

Preparation of a Composition Comprising Thymosin β4

The compositions shown in Table 1 below were prepared in accordance with the same procedures as described in Example 1. Unless otherwise indicated, numerical values in Table 1 have the unit of % (w/v) based on the total volume of the composition.

TABLE 1

|  | Thymosin β4 | Sodium citrate | Sodium acetate | Sodium ascorbate | Hydrochloric acid | Sodium hydroxide | Sterile purified water |
|---|---|---|---|---|---|---|---|
| Control | 0.1 | — | — | — | Added if required for adjusting to pH 7.0 | Added if require for adjusting to pH 7.0 | Amount necessary to make 100% (w/v) |
| Ex. 2 | 0.1 | 5.0 | — | — | | | |
| Ex. 3 | 0.1 | 10.0 | — | — | | | |
| Ex. 4 | 0.1 | — | 0.5 | — | | | |
| Ex. 5 | 0.1 | — | 1.5 | — | | | |
| Ex. 6 | 0.1 | — | 5.0 | — | | | |
| Ex. 7 | 0.1 | — | — | 0.5 | | | |
| Ex. 8 | 0.1 | — | — | 1.5 | | | |
| Ex. 9 | 0.1 | — | — | 5.0 | | | |

Further, the compositions shown in Table 2 below were prepared in accordance with the same procedures as described in Example 1. Unless otherwise indicated, numerical values in Table 2 have the unit of % (w/v) based on the total volume of the composition.

TABLE 2

|  | Thymosin β4 | Sodium citrate | Sodium acetate | Sodium ascorbate | Hydrochloric acid | Sodium hydroxide | Sterile purified water |
|---|---|---|---|---|---|---|---|
| Ex. 10 | 0.1 | 10.0 | 5.0 | — | Added if required for adjusting to pH 7.0 | Added if required for adjusting to pH 7.0 | Amount necessary to make 100% (w/v) |
| Ex. 11 | 0.1 | 10.0 | 1.5 | — | | | |
| Ex. 12 | 0.1 | 10.0 | — | 5.0 | | | |
| Ex. 13 | 0.1 | 10.0 | — | 1.5 | | | |
| Ex. 14 | 0.1 | 1.5 | 5.0 | — | | | |
| Ex. 15 | 0.1 | 1.5 | 1.5 | — | | | |
| Ex. 16 | 0.1 | 1.5 | — | 5.0 | | | |
| Ex. 17 | 0.1 | 1.5 | — | 1.5 | | | |

EXPERIMENTAL EXAMPLE 1

Cell Migration Experiment

A single cell layer was formed, by inoculating primary human corneal epithelial cells (HCEC)(ATCC, US) onto 6-well plate (Thermo, Ltd.) with $3 \times 10^5$ cells per well. Then, some scratches with similar sizes were formed at the middle of each well by using a 1 ml sterile pipette tip. After washing the wells with the culture medium to remove cell debris, the composition comprising thymosin β4 prepared in each of the above examples was added to the plate.

After 0 h, 6 h, 12 h and 24 h, each well was photographed with an inverted microscope combined with a digital camera. The size of scratch was decreased by cell migration and this was determined to show the treatment effects of the corneal injury.

Figure 1:
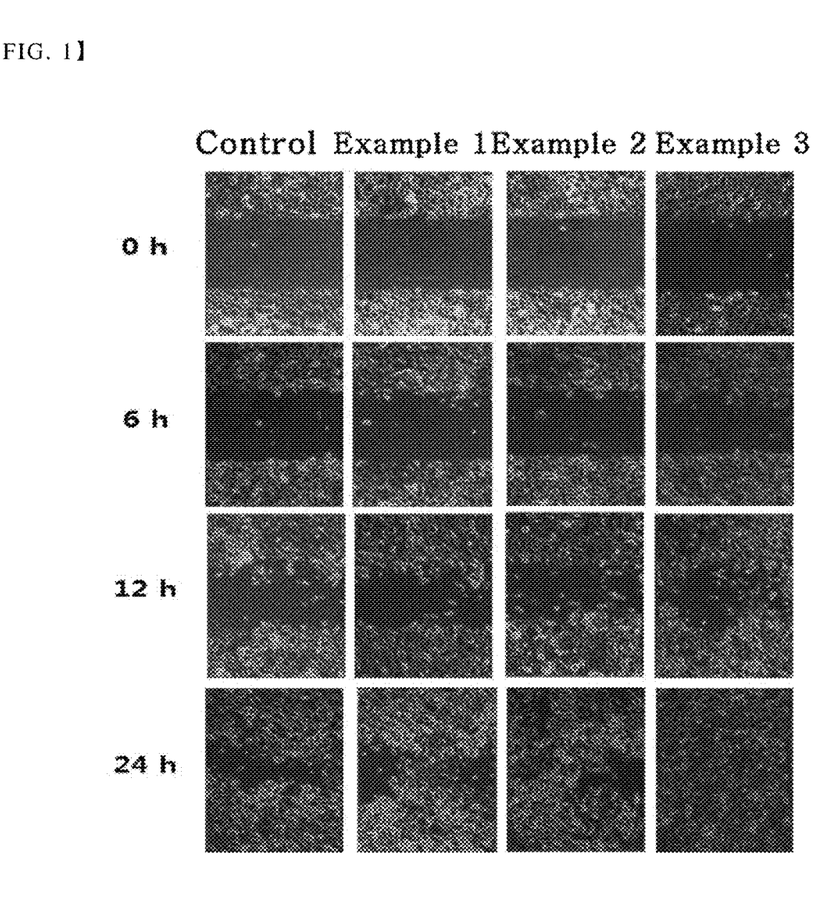
FIGS. 1 to 3 provide the results of cell migration after treating the cells with the compositions comprising thymosin β4 and an organic acid.
Figure 2:
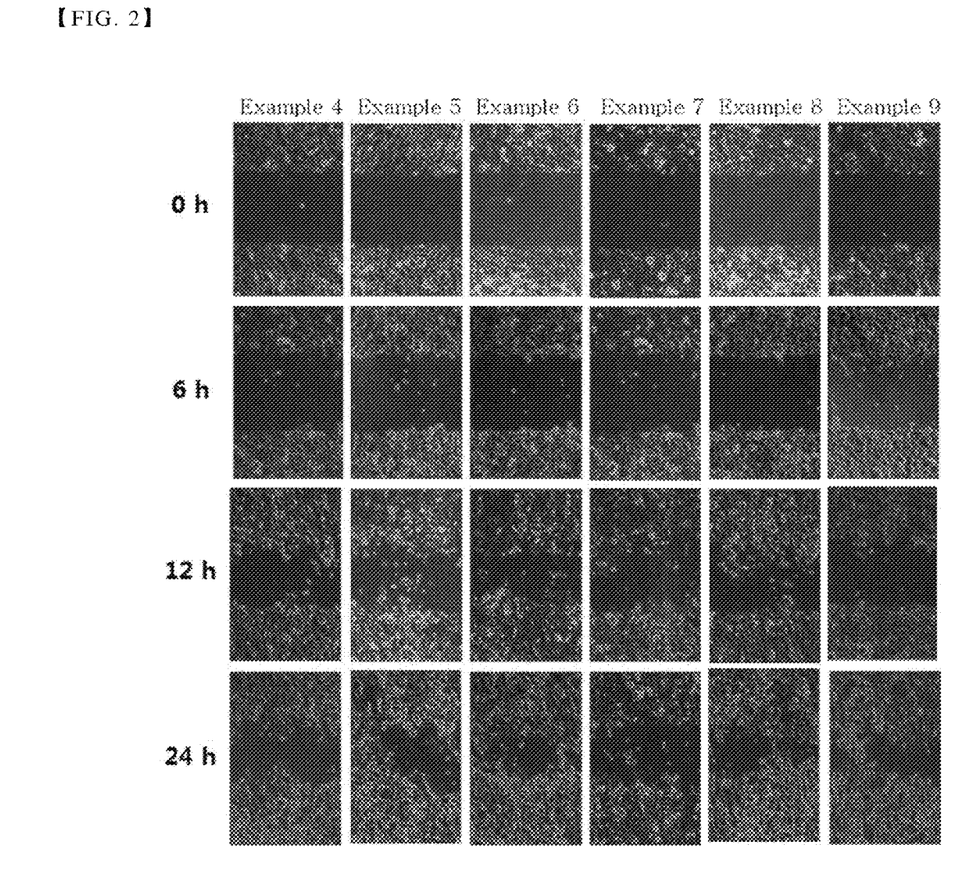
Figure 3:
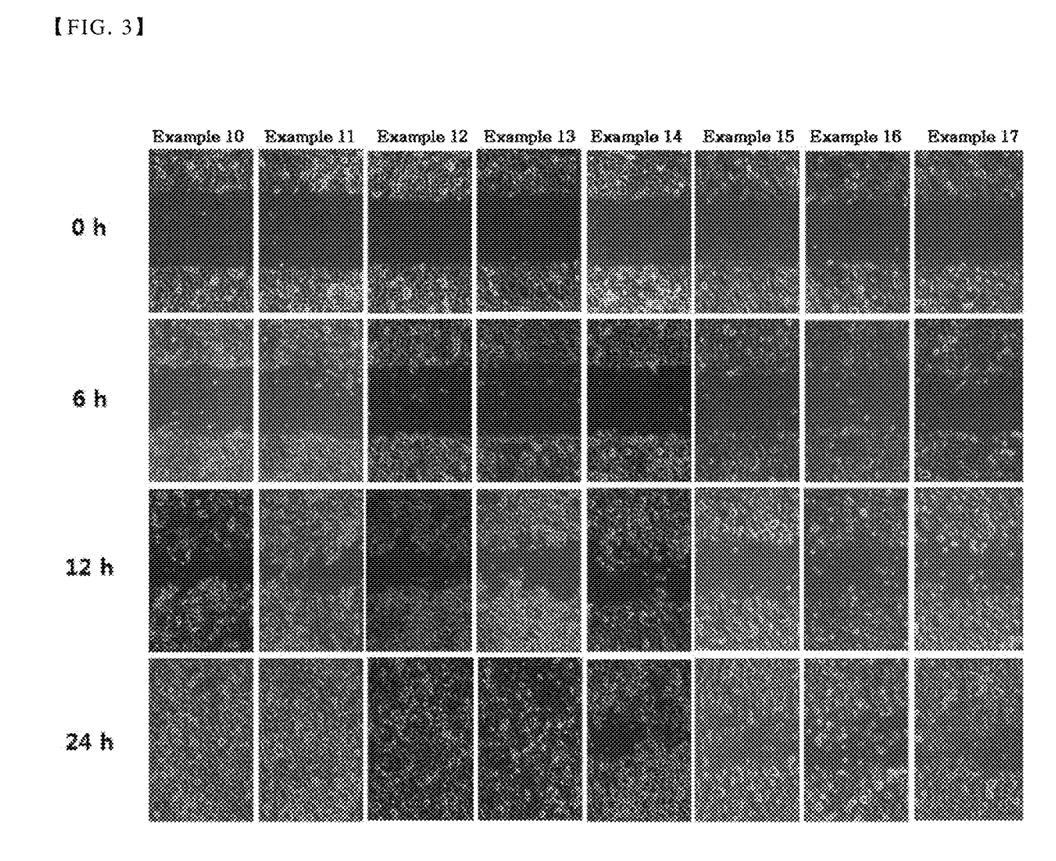

As shown in FIGS. 1 to 3, the results of the present experiments demonstrate that the compositions comprising citric acid together with thymosin β4 promoted cell migration, as compared with the composition comprising thymosin β4 alone as an active ingredient. Further, it was found that the compositions comprising thymosin β4, citric acid and acetic acid most noticeably promoted migration of corneal epithelial cells.

EXPERIMENTAL EXAMPLE 2

Cell Proliferation Experiment

In order to confirm whether the composition comprising thymosin β4 promotes proliferation of primary human corneal epithelial cells, cells were stained using CCK-8 kit (Dojindo, Japan). After inoculating $3 \times 10^3$ cells in 100 μL onto each well of a 96-well plate (Thermo, Ltd.), the compositions comprising thymosin β4 in accordance with Control, Example 1, Example 3, Example 6 and Example 10 were added on the plate.

12 h, 24 h and 48 h after administering the compositions comprising thymosin β4, 10 μl of CCK-8 reagent was added to the plate, followed by incubation at 37° C. for 2 hours. Optical density ($OD_{450}$) at 450 nm was measured by using a microplate reader.

Figure 4:
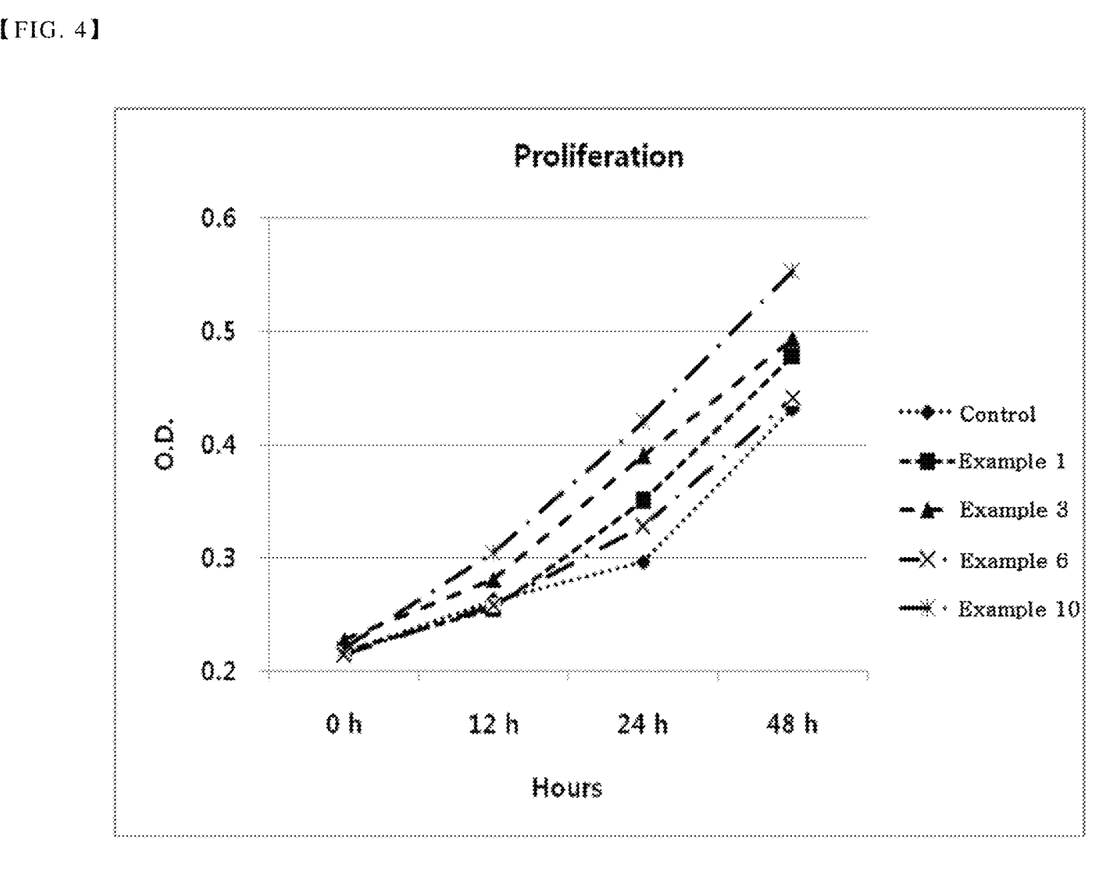
FIG. 4 presents the extent of cell proliferation in the cells treated with the compositions comprising thymosin β4 and an organic acid.

As a result, it was observed that the compositions comprising citric acid as well as thymosin β4, and the compositions comprising citric acid and acetic acid as well as thymosin β4 markedly promoted cell proliferation, as compared to the composition comprising thymosin β4 only (see FIG. 4).

EXPERIMENTAL EXAMPLE 3

Determination of Treatment Effects of Thymosin β4 Citric Acid and Mixture thereof in Animal Model 3.1. Preparation of Animal Model with Chemical Burns For experiments of wound treatment effects, 6 to 8-weeks old mice (BALB/c) were anesthetized with ether, and then a round filter paper (2 mm diameter) dipped in 1N NaOH contacted on the center of the cornea for 30 seconds to induce an injury in the corneal epithelium. After washing the injured part with 0.9% saline for 5 seconds, 0.9% saline, and the compositions in Example 3, Example 10 and Control were respectively dropped into the eye at 5 minutes after inducing the corneal injury. Thereafter, the above compositions and 0.9% saline were respectively dropped into the eye four times a day (20 μL/each time).

3.2. Examination of Myeloperoxidase (MPO) Activity

According to the methods reported in Exp. Eye Res., 1984, 39, 261-265 myeloperoxidase activity analysis was conducted on the cornea on which the above compositions (0.9% saline, Example 3, Example 10 and Control) were respectively administered in order to quantify PMN. The activity of MPO is proportionate to the number of PMN.

1, 7 and 14 days after the corneal injury, the cornea was removed from the mice to which the respective compositions (n=3/group, each time) were administered, chopped into small pieces in a vial containing 1 mL of 50 mM phosphate buffer (pH 6.0) with 0.5% hexadecyl trimethyl ammonium bromide (HTAB), and homogenized by means of a Polytron homogenizer on ice. After homogenization, the homogenizer was washed with the HTAB solution. The homogenate was adjusted to have 100 mg tissues per 1 mL by adding the HTAB solution thereto, and subjected to ultrasonication for 10 seconds, freezing and thawing three times, and centrifugation at 4° C. and 14,000 rpm. 0.1 mL of supernatant was mixed with 2.9 mL of 50 mM phosphate buffer (pH 6.0) containing 0.167 mg/mL o-diansidine dihydrochloride and 0.0005% hydrogen peroxide. A change in absorbance at 460 nm was determined by means of a UV spectrometer at 25° C. for 5 minutes. 1 Unit of MPO activity denoted degradation of 1 mol of peroxides per minute at 25° C.

Figure 5:
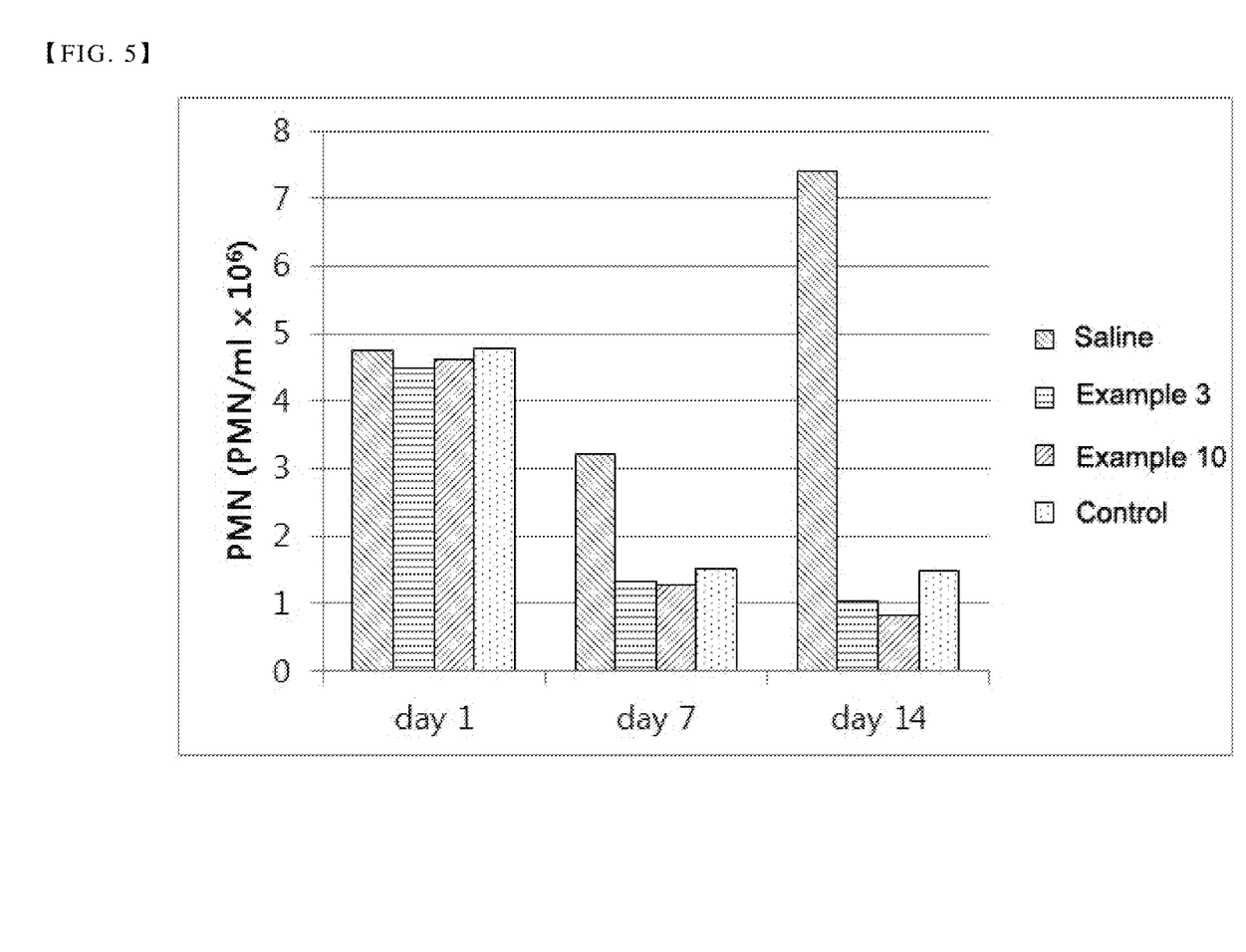
FIG. 5 shows the inhibitory effects of the present compositions on PMN infiltration.

As a result of the determination, it was confirmed that, as compared with the composition comprising saline or thymosin β4 only, the compositions comprising citric acid as well as thymosin β4, and the compositions comprising citric acid and acetic acid as well as thymosin β4 significantly inhibited PMN infiltration (see FIG. 5).

ingredient, to a subject in need thereof, wherein an amount of the thymosin β4 in the first composition ranges from 0.05 to 0.5% (w/v) based on the total volume of the first composition, and an amount of the citric acid or its salt in the second composition ranges from 1.0 to 10.0% (w/v) based on the total volume of the second composition.

2. The method according to claim 1, wherein the thymosin β4 is administered at a total daily dose of 0.08 to 2.0 ml of the first composition.

3. The method according to claim 1, wherein the citric acid or its salt is administered with a total daily dose of 0.1 to 4.0 ml of the second composition.

4. The method according to claim 1, wherein the first composition and the second composition are in a formulation selected from the group consisting of an aqueous solution, lotion, plaster, gel, cream, paste, spray, suspension, dispersion, ointment, and oil.

5. The method according to claim 4, wherein the first composition and the second composition have a pH 6.8-8.1.

6. The method according to claim 4, wherein the first composition and the second composition further comprise an ophthalmically acceptable carrier.

7. The method according to claim 6, wherein the carrier is one or more selected from the group consisting of alkanols, vegetable oils, and mineral oils.

8. The method according to claim 4, wherein the first composition and the second composition further comprise a tonicity agent.

9. The method according to claim 4, wherein the first composition and the second composition formulation further comprise a viscosity enhancer.

10. The method according to claim 1, wherein the first composition and the second composition are a same composition.

11. The method according to claim 1, wherein the first composition and the second composition are different from each other and administered simultaneously or sequentially.

What is claimed is:

1. A method for the treatment of a corneal injury, comprising administering (i) a first composition comprising thymosin β4 as an active ingredient and (ii) a second composition comprising citric acid or its salt, as an active 12. The method according to claim 1, wherein the first composition and/or the second composition further comprises acetic acid, ascorbic acid or a salt thereof.

* * * * *

SEQUENCE LISTING

```
<160> NUMBER OF SEQ ID NOS: 1

<210> SEQ ID NO 1
<211> LENGTH: 43
<212> TYPE: PRT
<213> ORGANISM: Artificial Sequence
<220> FEATURE:
<223> OTHER INFORMATION: synthetic construct of thymosin beta 4

<400> SEQUENCE: 1

Ser Asp Lys Pro Asp Met Ala Glu Ile Glu Lys Phe Asp Lys Ser Lys
  1               5                  10                  15

Leu Lys Lys Thr Glu Thr Gln Glu Lys Asn Pro Leu Pro Ser Lys Glu
             20                  25                  30

Thr Ile Glu Gln Glu Lys Gln Ala Gly Glu Ser
         35                  40
```